United States Patent [19]

Isogai et al.

[11] 4,243,599

[45] Jan. 6, 1981

[54] PROCESS FOR SIMULTANEOUSLY PRODUCING P-TOLUIC ACID AND ALKYLENE OXIDE

[75] Inventors: Nobuo Isogai; Takashi Okawa; Takako Takeda, all of Niigata, Japan

[73] Assignee: Mitsubishi Gas Chemical Company, Inc., Tokyo, Japan

[21] Appl. No.: 696,761

[22] Filed: Jun. 16, 1976

[30] Foreign Application Priority Data

Jun. 30, 1975 [JP] Japan .................................. 50-80734

[51] Int. Cl.³ ........................................... C07D 301/14
[52] U.S. Cl. ........................... 260/348.25; 260/502 A
[58] Field of Search ...................... 260/348.5 L, 348.25

[56] References Cited

U.S. PATENT DOCUMENTS

| | | | |
|---|---|---|---|
| 3,341,556 | 9/1967 | Stautzenberger et al. | 260/348.5 L |
| 3,476,776 | 11/1969 | Sennewald et al. | 260/348.5 L |

FOREIGN PATENT DOCUMENTS

| | | | |
|---|---|---|---|
| 1165009 | 3/1964 | Fed. Rep. of Germany | 260/502 A |
| 906970 | 9/1962 | United Kingdom . | |
| 906971 | 9/1962 | United Kingdom . | |
| 978662 | 12/1964 | United Kingdom . | |
| 1282775 | 7/1972 | United Kingdom | 260/348.5 L |

OTHER PUBLICATIONS

Daniel Swern, Organic Peroxides, vol. 1 (1971), pp. 364–366, 467–468.

*Primary Examiner*—Norma S. Milestone
*Attorney, Agent, or Firm*—Armstrong, Nikaido, Marmelstein & Kubovcik

[57] ABSTRACT p-Toluic acid and alkylene oxide are produced simultaneously in high yields by epoxidizing a lower olefin such as ethylene or propylene with per-p-toluic acid in the presence of 10 to 1,000 ppm by weight, preferably 50 to 500 ppm by weight of at least one of 8-hydroxyquinoline, dipicolinic acid, and pyridine-2,6-dimethanol, as a stabilizer for peracid at a reaction temperature of 30° to 120° C., preferably 40° to 100° C. Per-p-toluic acid is in the form of a solution containing 10 to 50% by weight of per-p-toluic acid.

11 Claims, No Drawings

PROCESS FOR SIMULTANEOUSLY PRODUCING P-TOLUIC ACID AND ALKYLENE OXIDE

This invention relates to a process for simultaneously producing p-toluic acid and alkylene oxide by epoxidizing a lower olefin with per-p-toluic acid, and more particularly to a process for simultaneously producing p-toluic acid and alkylene oxide in good yield by epoxidizing a lower olefin with per-p-toluic acid in the presence of at least one of 8-hydroxyquinoline, dipicolinic acid and pyridine-2,6-dimethanol.

Generally, per-p-toluic acid is obtained by autooxidation of p-tolualdehyde synthesized from cheap and abundantly available toluene and carbon monoxide in the presence of a catalyst such as $HF-BF_3$, $HCl-AlCl_3$, etc. according to Gattermann-Koch reaction, with an oxygen-containing gas.

That the per-p-toluic acid thus obtained is used in oxidation of other compounds is known, for example, from Japanese Patent Publication No. 13506/72.

According to the present invention, a lower olefin, especially ethylene or propylene, is epoxidized with the per-p-toluic acid to produce an alkylene oxide serving as a raw material for producing polyester, polyurethane, etc. and p-toluic acid serving as a raw material for producing terephthalic acid at the same time. Thus, the present invention has a great industrial significance in this respect, and also a distinguished value in the effective utilization of resources.

Per-p-toluic acid can be prepared oxidizing p-tolualdehyde with an oxygen-containing gas such as air in a solution of 10 to 50% by weight, preferably 10 to 40% by weight, of an aliphatic ketone such as acetone or methylethylketone, or a fatty acid ester such as ethyl acetate at a reaction temperature of 10° to 50° C. under a pressure of 1 to 60 kg/cm² gage, preferably 20 to 40 kg/cm² gage. In that case, salts of iron, cobalt, nickel, copper, chromium, vanadium, etc. or compounds of the elements belonging to the periodic table, groups IIb, III, IV, etc. are used as an oxidation catalyst, and cobalt salts are especially effective. For example, 1 to 20 ppm, preferably 2 to 6 ppm, of cobaltous chloride or cobaltous acetate is added to the p-tolualdehyde solution in terms of Co. The entire amount of p-tolualdehyde can undergo reaction in a reaction time of 1 to 2 hours thereby, and per-p-toluic acid can be obtained in yield of 70 to 95% by mole.

However, said oxidation catalyst disadvantageously acts as a catalyst for decomposing per-p-toluic acid at the same time as it acts to promote the oxidation of p-tolualdehyde. Therefore, when the per-p-toluic acid product solution obtained by oxidizing p-tolualdehyde in the presence of said oxidation catalyst is used directly as an epoxidizing agent for olefin, a proportion of unutilized per-p-toluic acid in the epoxidation reaction of olefin is increased, causing to considerably reduce an alkylene oxide yield based on per-p-toluic acid. Furthermore, by-products such as glycol ester of p-toluic acid, etc. are liable to be produced, and thus p-toluic acid yield is also lowered. Therefore, when the oxidation catalyst is used for the production of per-p-toluic acid, it is necessary to remove the oxidation catalyst from the per-p-toluic acid product solution, or to recover per-p-toluic acid from the per-p-toluic acid product solution before carrying out the epoxidation reaction. However, no process has been available for removing the catalyst from the per-p-toluic acid product solution through simple operations without decomposing the per-p-toluic acid, or it is also impossible to separate the per-p-toluic acid from the product solution by distillation. It is possible to separate the per-p-toluic acid therefrom by crystallization, but the crystallization procedure is very complicated, and has such a disadvantage as a part of the per-p-toluic acid is decomposed. That is, it is very difficult to separate the per-p-toluic acid and the oxidation catalyst from each other in an inductual scale.

The present inventors have extensively studied a process for adding a stabilizer for peracid to the per-p-toluic acid product solution containing such oxidation catalyst to prevent the inconvenience appearing in the epoxidation of olefin by the per-p-toluic acid product solution, and as a result have found that such inconvenience can be overcome by adding some kind of the stabilizer for peracid to the product solution, and p-toluic acid and alkylene oxide can be produced in high yields at the same time, and have completed the present invention. Furthermore, the present inventors have found the alkylene oxide and p-toluic acid can be produced in better yields when said stabilizer for peracid is added thereto even in the epoxidation of a lower olefin by the per-p-toluic acid containing none of such oxidation catalyst than when no stabilizer for peracid is added thereto.

Now, the present invention will be described in detail below.

In the present invention, the per-p-toluic acid product solution obtained by auto-oxidizing p-tolualdehyde with an oxygen-containing gas in a solvent of aliphatic ketone such as acetone or methylethylketone or fatty acid such as ethyl acetate ester with or without an oxidation catalyst, or a solution of per-p-toluic acid solution in aliphatic ketone such as acetone or methylethylketone or fatty acid ester such as ethyl acetate are used, and will be hereinafter referred to as "per-p-toluic acid solution". The per-p-toluic acid concentration in the per-p-toluic acid solution is 10 to 50% by weight, preferably 10 to 40% by weight. The per-p-toluic acid concentration of less than 10% by weight is not preferable, because the epoxidation reaction is retarded, whereas the per-p-toluic acid concentration of more than 50% by weight is also not preferable, because the per-p-toluic acid cannot be dissolved in the solvent.

As the stabilizer for peracid, at least one of 8-hydroxyquinoline, dipicolinic acid and pyridine-2,6-dimethanol is used in the present invention. Among these three compounds, dipicolinic acid is particularly preferable. Generally, these compounds are well known as the stabilizer for peracid (see, for example, British Patent No. 906,971). However, these three compounds are very effective for obtaining p-toluic acid and alkylene oxide in high yields at the same time by epoxidizing a lower olefin by per-p-toluic acid, as compared with other stabilizer for peracid, for example, polyphosphates, EDTA, diethylenetriamine pentaacetate, potassium thiocyanate, polyaminocarboxylic acid, picolinic acid, alkyl esters of pyrophosphoric acid, etc.

In the present invention, 10 to 1,000 ppm by weight, preferably 50 to 500 ppm by weight of the stabilizer for peracid is used on the basis of the per-p-toluic acid solution.

The lower olefin to be epoxidized is not particularly restricted in the present invention, but ethylene and propylene are preferable. Furthermore it is preferable, in view of effective utilization of per-p-toluic acid, to use at least an equimolar amount of the lower olefin to the per-p-toluic acid, but it is not particularly effective to use the lower olefin in moles more than 4 times those of the per-p-toluic acid.

The present invention is carried out at a reaction temperature of 30° to 120° C., preferably 40° to 100° C. under a pressure of 1 to 60 kg/cm$^2$ gage, preferably 5 to 20 kg/cm$^2$ gage by adding said stabilizer for peracid to the per-p-toluic acid solution, and charging the lower olefin thereto, while thoroughly stirring the solution in the closed system. The reaction rate is low below 30° C., whereas the decomposition of per-p-toluic acid is liable to take place above 120° C., lowering the yields in the epoxidation reaction.

According to the present invention, the reaction is completed within two hours, and the alkylene oxide can be obtained in yield of more than 80% by mole, and p-toluic acid in yield of almost 100% by mole, on the basis of per-p-toluic acid. That is, all the amount of per-p-toluic acid is consumed in the reaction, and are converted to p-toluic acid, where more than 80% by mole of per-p-toluic acid is effectively utilized in the epoxidation of the lower olefin. Thus, the desired alkylene oxide and p-toluic acid can be obtained readily in high yields in the present invention.

Furthermore, it is a remarkable feature of the present invention that substantially no other by-products than the desired products are produced. That is, the addition of the stabilizer for peracid inhibits the ring-opening reaction of the alkylene oxide, and such by-products as esters of p-toluic acid, etc. are hardly produced.

The products resulting from the epoxidation reaction can be readily separated and recovered. For example, when propylene is used as the olefin, the unreacted propylene can be separated and recovered by distillation under increased pressure; propylene oxide by distillation under the atmospheric pressure; the solvent used by simple distillation; and p-toluic acid by crystallization or, if necessary, by distillation under reduced pressure.

As described above, in the present invention, p-toluic acid and alkylene oxide having a great industrial demand and value can be readily and effectively obtained in high yields from per-p-toluic acid derived from toluene having less industrial applications, and thus the present invention provides an important significance to the industry.

The present invention is not restricted to a batch process, but can be, of course, carried out in a continuous manner.

Now, the present invention will be described in detail below, referring to Examples and Comparative Examples.

EXAMPLE 1

200 g of per-p-toluic acid product solution containing 23% by weight of per-p-toluic acid, obtained by oxidizing p-tolualdehyde in the presence of acetone as a solvent without any catalyst was admixed with 500 ppm by weight of dipicolinic acid based on the product solution, and the resulting solution was then charged into an autoclave having a capacity of 500 ml and a rotating stirrer.

The charged solution contained 46 g (0.302 moles) of per-p-toluic acid, 152.2 g of acetone as the solvent, 1.86 g (0.014 moles) of p-toluic acid, and dipicolinic acid.

Then, 50.5 g (1.20 moles) of propylene, which corresponded to 4 times the moles of the per-p-toluic acid, was charged to the autoclave, and the autoclave was tightly closed. Reaction was carried out at a reaction temperature of 70° C. under a pressure of 12.8 to 11.4 kg/cm$^2$ gage for one hour with stirring.

Then, the autoclave was cooled, and the unreacted propylene was purged from the system. The content of the autoclave was taken out, and the entire amount of the content was subjected to distillation operation, whereby 16.7 g (0.288 moles) of propylene oxide, and after recovery of the solvent acetone, 43.0 g of p-toluic acid were obtained. Thus, the selectivity (yield) to propylene oxide was 95.4% by mole, on the basis of per-p-toluic acid, whereas the p-toluic acid formed by the reaction amounted to 41.14 g (0.302 moles) by deduction of the amount of the p-toluic acid contained originally in the charged solution, and thus the selectivity (yield) to p-toluic acid was 100% by mole on the basis of per-p-toluic acid.

EXAMPLE 2

150 g of per-p-toluic acid product solution containing 20.5% by weight of per-p-toluic acid, obtained by oxidizing p-tolualdehyde in the presence of acetone as a solvent with 5.4 ppm by weight of a cobaltous chloride catalyst in terms of Co was admixed with 150 ppm by weight of dipicolinic acid based on the product solution, and the resulting solution was subjected to epoxidation of propylene in an autoclave as used in Example 1.

The charged solution contained 30.75 g (0.202 moles) of per-p-toluic acid, 117.8 g of acetone as the solvent, 1.42 g (0.010 mole) of p-toluic acid, and dipicolinic acid. 34.7 g (0.824 moles) of propylene was then changed to the autoclave, and reaction was carried out at a reaction temperature of 50° C. under a pressure of 9.8 to 8.8 kg/cm$^2$ gage for one hour with stirring.

After the reaction was conducted, the autoclave was cooled, and the unreacted propylene was purged from the system. Then, the content was taken out of the autoclave, and the entire amount of the content was subjected to distillation operation, whereby 10.8 g (0.186 moles) of propylene oxide, and after the recovery of the solvent acetone, 28.9 g of p-toluic acid were obtained.

Thus, selectivity to propylene oxide was 92.1% by mole on the basis of per-p-toluic acid, whereas the p-toluic acid formed by the reaction amounted to 27.48 g (0.202 moles) by deduction of the amount of the p-toluic acid contained originally in the charged solution, that is, selectivity to p-toluic acid was 100% by mole on the basis of per-p-toluic acid.

EXAMPLE 3

150 g of per-p-toluic acid product solution containing 19.9% by weight of per-p-toluic acid, obtained by oxidizing p-tolualdehyde in the presence of acetone as a solvent with 5.4 ppm by weight of cobaltous chloride catalyst in terms of Co was admixed with 150 ppm by weight of 8-hydroxyquinoline based on the product solution, and the resulting solution was subjected to epoxidation of propylene in an autoclave as used in Example 1.

The charged solution contained 29.85 g (0.196 moles) of per-p-toluic acid, 118.5 g of acetone as the solvent, 1.64 g (0.012 moles) of p-toluic acid, and 8-hydroxyquinoline, and then 34.5 g (0.819 moles) of propylene was charged to the autoclave. Reaction was carried out at a reaction temperature of 50° C. under a pressure of 9.7 to 8.8 kg/cm$^2$ gage for one hour with stirring.

After the reaction was conducted, the autoclave was cooled, and the unreacted propylene was purged from the autoclave, and the content was taken out of the autoclave. The entire amount of the content was subjected to distillation operation, whereby 10.4 g (0.179 moles) of propylene oxide, and after the recovery of the solvent acetone, 27.9 g of p-toluic acid were obtained.

Thus, selectivity to propylene oxide was 91.3% by mole on the basis of per-p-toluic acid, whereas the p-toluic acid formed by the reaction amounted to 26.26 g (0.193 moles) by deduction of the amount of the p-toluic acid contained originally in the charged solution, and thus selectivity to p-toluic acid was 98.5% by mole on the basis of per-p-toluic acid.

EXAMPLE 4

150 g of per-p-toluic acid product solution containing 21% by weight of per-p-toluic acid, obtained by oxidizing p-tolualdehyde in the presence of ethyl acetate as a solvent with 5.4 ppm by weight of cobaltous acetate catalyst in terms of Co, was admixed with 150 ppm by weight of dipicolinic acid based on the product solution, and the resulting solution was subjected to epoxidation of propylene in an autoclave as used in Example 1.

The charged solution contained 31.5 g (0.207 moles) of per-p-toluic acid, 113 g of ethyl acetate as the solvent, 5.61 g (0.041 mole) of p-toluic acid, and dipicolinic acid, and then 34.2 g (0.812 moles) of propylene was charged to the autoclave. Reaction was carried out at a reaction temperature of 50° C. under a pressure of 11.7 to 10.6 kg/cm² gage for one hour with stirring.

After the reaction was conducted, the autoclave was cooled, and the entire amount of the content was subjected to distillation operation, whereby 10.6 g (0.183 moles) of propylene oxide, and after the recovery of the solvent ethyl acetate, 33.0 g of p-toluic acid were obtained. Thus, selectivity to propylene oxide was 88.4% by mole on the basis of per-p-toluic acid, whereas the p-toluic acid formed by the reaction amounted to 27.39 g (0.201 mole) by deduction of the amount of the p-toluic acid contained originally in the charged solution, and selectivity to p-toluic acid was 97.1% by mole on the basis of per-p-toluic acid.

EXAMPLE 5

150 g of per-p-toluic acid product solution containing 20.1% by weight of per-p-toluic acid, obtained by oxidizing p-tolualdehyde in the presence of acetone as a solvent with 5.4 ppm by weight of cobaltous chloride catalyst in terms of Co, was admixed with 200 ppm by weight of pyridine-2,6-dimethanol based on the product solution, and the resulting solution was subjected to epoxidation of propylene in an autoclave as in Example 1.

The charged solution contained 30.15 g (0.198 moles) of per-p-toluic acid, 118.2 g of acetone as the solvent, 1.50 g (0.011 mole) of p-toluic acid, and pyridine-2,6-dimethanol, and then 34.0 g (0.808 moles) of propylene was charged to the autoclave. Reaction was carried out at a reaction temperature of 70° C. under a pressure of 12.1 to 10.9 kg/cm² gage for 0.5 hours with stirring.

After the reaction was conducted, the autoclave was cooled, and the entire amount of the content in the autoclave was subjected to distillation operation, whereby 10.3 g (0.177 moles) of propylene oxide, and after the recovery of the solvent acetone, 27.9 g of p-toluic acid were obtained.

Thus, selectivity to propylene oxide was 89.4% by mole on the basis of per-p-toluic acid, whereas the p-toluic acid formed by the reaction amounted to 26.4 g (0.194 moles) by deduction of the amount of the p-toluic acid contained originally in the charged solution, and selectivity to p-toluic acid was 98.0% by mole on the basis of per-p-toluic acid.

COMPARATIVE EXAMPLE 1
(CORRESPONDING TO EXAMPLE 1)

200 g of per-p-toluic acid product solution containing 23% by weight of per-p-toluic acid, obtained by oxidizing p-tolualdehyde in the presence of acetone as a solvent without any catalyst, was directly subjected to epoxidation of propylene in an autoclave as used in Example 1. The charged solution contained 46 g (0.302 moles) of per-p-toluic acid, 152.2 g of acetone as a solvent, and 1.86 g (0.014 moles) of p-toluic acid, and then 50.7 g (1.20 mole) of propylene was charged to the autoclave. Reaction as carried out at a reaction temperature of 70° C. under a pressure of 12.8 to 11.5 kg/cm² gage for one hour with stirring.

After the reaction was conducted the autoclave was cooled, and the unreacted propylene was purged from the system. Then, the content was taken out of the autoclave, and the entire amount of the content was subjected to distillation operation, whereby 15.9 g (0.274 moles) of propylene oxide, and after the recovery of the solvent acetone, 42.2 g of p-toluic acid were obtained.

Thus, selectivity to propylene oxide was 90.7% by mole on the bases of per-p-toluic acid, whereas the p-toluic acid formed by the reaction amounted to 40.34 g (0.296 moles) by deduction of the amount of the p-toluic acid contained originally in the charged solution, and selectivity to p-toluic acid was 98.1% by mole on the basis of per-p-toluic acid.

COMPARATIVE EXAMPLE 2
(CORRESPONDING TO EXAMPLE 2)

150 g of per-p-toluic acid product solution containing 20.5% by weight of per-p-toluic acid, obtained by oxidizing p-tolualdehyde in the presence of acetone as a solvent with 5.4 ppm by weight of cobaltous chloride catalyst in terms of Co, was directly subjected to epoxidation of propylene in an autoclave as used in Example 1. The charged solution contained 30.75 g (0.202 moles) of per-p-toluic acid, 117.8 g of acetone as a solvent, and 1.42 g (0.10 mole) of p-toluic acid, and then 34.5 g (0.819 moles) of propylene was charged to the autoclave. Reaction was carried out at a reaction temperature of 50° C. under a pressure of 9.7 to 9.1 kg/cm² gage for one hour with stirring.

After the reaction was conducted, the autoclave was cooled, and the unreacted propylene was purged from the system. Then, the content was taken out of the autoclave, and the entire amount of the content was subjected to distillation operation, whereby 7.11 g (0.122 moles) of propylene oxide, and after the recovery of the solvent acetone, 26.8 g of p-toluic acid were obtained.

Thus, selectivity to propylene oxide was 60.4% by mole on the basis of per-p-toluic acid, whereas the p-toluic acid formed by the reaction amounted to 25.38 g (0.186 moles) by deduction of the amount of the p-toluic acid contained originally in the charged solution, and selectivity to p-toluic acid was 92.1% by mole on the basis of per-p-toluic acid.

COMPARATIVE EXAMPLE 3
(CORRESPONDING TO EXAMPLE 5)

Reaction was carried out at a reaction temperature of 70° C. in Comparative Example 2, and the reaction was completed in 0.5 hours. Selectivities to propylene oxide and p-toluic acid were 42% by mole and 88% by mole, respectively, on the basis of per-p-toluic acid.

COMPARATIVE EXAMPLE 4
(CORRESPONDING TO EXAMPLE 1)

150 g of per-p-toluic acid product solution containing 21.2% by weight of per-p-toluic acid, obtained by oxidizing p-tolualdehyde in the presence of acetone as a solvent without any catalyst, was admixed with 150 ppm by weight of disodium ethylenediamine tetraacetate dihydrate based on the product solution, and the resulting solution was subjected to epoxidation of propylene in an autoclave as used in Example 1.

The charged solution contained 31.8 (0.209 moles) of per-p-toluic acid, 117.1 g of acetone as the solvent, 1.1 g (0.008 moles) of p-toluic acid, and disodium ethylenediamine tetraacetate dihydrate, and then 35.5 g (0.843 moles) of propylene was charged to the solution. Reaction was carried out at a reaction temperature of 70° C. under a pressure of 12.3 to 10.9 kg/cm'gage for one hour with stirring.

After the reaction was conducted, the autoclave was cooled, and the unreacted propylene was purged from the system. Then, the content was taken out of the autoclave, and the entire amount of the content was subjected to distillation operation, whereby 11.1 g (0.191 mole) of propylene oxide, and, after the recovery of the solvent acetone, 29.0 g of p-toluic acid were obtained.

Thus, selectivity to propylene oxide was 91.4% by mole on the basis of per-p-toluic acid, whereas the p-toluic acid formed by the reaction amounted to 27.9 g (0.205 moles) by deduction of the amount of the p-toluic acid contained originally in the charged solution, and selectivity to p-toluic acid was 98.1% by mole on the basis of per-p-toluic acid.

COMPARATIVE EXAMPLE 5
(CORRESPONDING TO EXAMPLE 2)

150 g of per-p-toluic acid product solution containing 21.0% by weight of per-p-toluic acid, obtained by oxidizing p-tolualdehyde in the presence of acetone as a solvent with 5.4 ppm by weight of cobaltous chloride catalyst in terms of Co, was admixed with 200 ppm by weight of sodium pyrophosphate based on the product solution, and the resulting solution was subjected to epoxidation of propylene in an autoclave as used in Example 1.

The charged solution contained 31.5 (0.207 moles) of per-p-toluic acid, 117.2 g of acetone as the solvent, 1.3 g (0.010 mole) of p-toluic acid, and sodium pyrophosphate. Then, 34.5 g (0.819 moles) of propylene was charged to the solution, and reaction was carried out at a reaction temperature of 50° C. under a pressure of 9.7 to 9.1 kg/cm² gage for one hour with stirring.

After the reaction was conducted, the autoclave was cooled, and the unreacted propylene was purged from the system. Then, the content was taken out of the autoclave, and the entire amount of the content was subjected to distillation operation, whereby 7.5 g (0.129 moles) or propylene oxide, and, after the recovery of the solvent acetone, 28.0 g of p-toluic acid were obtained.

Thus, selectivity to propylene oxide was 62.3% by mole on the basis of per-p-toluic acid, whereas the p-toluic acid formed by the reaction amounted to 26.7 g (0.196 moles) by deduction of the amount of p-toluic acid contained originally in the charged solution, and selectivity to p-toluic acid was 94.7% by mole on the basis of per-p-toluic acid.

COMPARATIVE EXAMPLE 6
(CORRESPONDING TO EXAMPLE 2)

150 g of per-p-toluic acid product solution containing 21.0% by weight of per-p-toluic acid, obtained by oxidizing p-tolualdehyde in the presence of acetone as a solvent with 5.4 ppm by weight of cobaltous chloride catalyst in terms of Co, was admixed with 200 ppm by weight of picolinic acid based on the product solution, and the resulting solution was subjected to epoxidation of propylene in an autoclave as used in Example 1.

The charged solution contained 31.5 g (0.207 moles) of per-p-toluic acid, 117.3 g of acetone as the solvent, 1.2 g (0.009 moles) of p-toluic acid, and picolinic acid. Then, 34.8 (0.827 moles) of propylene was charged to the solution, and reaction was carried out at a reaction temperature of 50° C. under a pressure of 9.9 to 9.1 kg/cm² gage for one hour with stirring.

After the reaction was conducted, the autoclave was cooled, and the unreacted propylene was purged from the system. Then, the content was taken out of the autoclave, and the entire amount of the content was subjected to distillation operation, whereby 7.3 g (0.126 moles) of propylene oxide, and after the recovery of the solvent acetone, 26.9 g of p-toluic acid were obtained.

Thus, selectivity to propylene oxide was 60.9% by mole on the basis of per-p-toluic acid, whereas the p-toluic acid formed by the reaction amounted to 25.7 g (0.189 moles) by deduction of the amount of p-toluic acid contained originally in the charged solution, and selectivity to p-toluic acid was 91.3% by mole on the basis of per-p-toluic acid.

What is claimed is:

1. A process for simultaneously producing p-toluic acid and an alkylene oxide by epoxidizing a lower olefin with per-p-toluic acid, which comprises adding dipicolinic acid as a stabilizer for peracid to a per-p-toluic acid solution.

2. A process according to claim 1, wherein 10 to 1,000 ppm by weight of the stabilizer for peracid is added to the per-p-toluic acid solution.

3. A process according to claim 2, wherein 50 to 500 ppm by weight of the stabilizer for peracid is added to the per-p-toluic acid solution.

4. A process for simultaneously producing p-toluic acid and alkylene oxide by expoxidizing a lower olefin with per-p-toluic acid in the presence of a solvent which comprises adding 10 to 1,000 ppm by weight of dipicolinic acid as a stabilizer for peracid to a per-p-toluic acid solution, adding a lower olefin to the resulting solution, subjecting the solution to epoxidation at a reaction temperature of 30° to 120° C. with stirring under a pressure of 1 to 60 kg/cm² gage, and recovering p-toluic acid and alkylene oxide from the system.

5. A process according to claim 4, wherein the solvent is aliphatic ketone or fatty acid ester.

6. A process according to claim 4, wherein 50 to 500 ppm of the stabilizer for peracid is added to the per-p-toluic acid solution.

7. A process according to claim 3, wherein 1 to 4 parts by mole of the lower olefin is added to the per-p-toluic acid solution per one part by mole of per-p-toluic acid.

8. A process according to claim 7, wherein the lower olefin is ethylene or propylene.

9. A process according to claim 4, wherein the epoxidation is carried out at a temperature of 40° to 100° C.

10. A process according to claim 4, wherein the per-p-toluic acid solution contains 10 to 50% by weight of per-p-toluic acid.

11. A process according to claim 4, wherein the per-p-toluic acid solution is a product solution obtained by autoxidation of p-tolualdehyde with an oxygen-containing gas in the presence of an aliphatic ketone or fatty acid ester as a solvent.

* * * * *